US009056002B2

(12) United States Patent
Tabor

(10) Patent No.: US 9,056,002 B2
(45) Date of Patent: Jun. 16, 2015

(54) STENT-GRAFT AND METHOD FOR PERCUTANEOUS ACCESS AND CLOSURE OF VESSELS

(71) Applicant: Medtronic, Inc., Minneapolis, MN (US)

(72) Inventor: Charles Tabor, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 434 days.

(21) Appl. No.: 13/654,662

(22) Filed: Oct. 18, 2012

(65) Prior Publication Data

US 2014/0114391 A1 Apr. 24, 2014

(51) Int. Cl.

*A61F 2/06* (2013.01)
*A61F 2/07* (2013.01)
*A61F 2/958* (2013.01)

(52) U.S. Cl.

CPC . *A61F 2/07* (2013.01); *A61F 2/958* (2013.01); *A61F 2002/061* (2013.01); *A61F 2002/075* (2013.01)

(58) Field of Classification Search

CPC .................... A61F 2002/061; A61F 2002/075; A61F 2/07; A61F 2/2427; A61F 2/24; A61F 2/954; A61F 2/856; A61F 2/95; A61F 2002/065

USPC .............. 623/1.11–1.13, 1.23, 2.11; 606/108; 128/898

See application file for complete search history.

(56) References Cited

U.S. PATENT DOCUMENTS

| | | | | |
|---|---|---|---|---|
| 5,725,552 | A | 3/1998 | Kotula et al. | |
| 5,843,167 | A | 12/1998 | Dwyer et al. | |
| 5,902,334 | A | 5/1999 | Dwyer et al. | |
| 5,944,738 | A | 8/1999 | Amplatz et al. | |
| 5,961,546 | A | 10/1999 | Robinson et al. | |
| 2006/0265056 | A1 | 11/2006 | Nguyen et al. | |
| 2007/0239266 | A1 | 10/2007 | Birdsall | |
| 2007/0239269 | A1 | 10/2007 | Dolan et al. | |
| 2008/0262590 | A1 | 10/2008 | Murray | |
| 2011/0251664 | A1 | 10/2011 | Acosta De Avecedo | |
| 2011/0251680 | A1 | 10/2011 | Tran et al. | |
| 2011/0264201 | A1 | 10/2011 | Yeung et al. | |
| 2012/0221089 | A1 * | 8/2012 | Drasler | 623/1.11 |

* cited by examiner

*Primary Examiner* — Katherine M Shi

(57) ABSTRACT

In a method of accessing and closing a vessel, a vessel is percutaneously accessed through a first opening in the vessel wall at a first location. A stent-graft is delivered through the first opening to a second location. The stent-graft is deployed at the second location. The vessel is then accessed through a second opening through the vessel wall at the second location, wherein the second opening is generally aligned with a fenestration through the graft material of the stent-graft. A delivery device is advanced through the second opening, the fenestration, and the stent-graft lumen to a third location spaced from the first location and the second location. After the delivery device is retracted through the lumen of the stent-graft and out of the fenestration and the second opening, the stent graft is rotated or translated such that the fenestration is not aligned with the second opening.

17 Claims, 8 Drawing Sheets

112 120 102 100 104 114 107 106 110 108

217 400 214 120 100 204 202 400 402 226

STENT-GRAFT AND METHOD FOR PERCUTANEOUS ACCESS AND CLOSURE OF VESSELS

FIELD OF THE INVENTION

The invention is related in general to n apparatus and method for providing percutaneous access to and closure of a blood vessel and, in particular, to the subclavian artery.

BACKGROUND OF THE INVENTION

Percutaneous access for procedures in body lumens such as blood vessels is desirable to minimize complications from surgical procedures. Procedures using percutaneous access are also referred to as minimally invasive procedures. Many percutaneous procedures involving the aorta, coronary arteries, or other vessels near the heart rely on percutaneous access via the femoral artery. Access via the femoral artery is preferred for transcatheter aortic valve implantation (TAVI) procedures since it enables the clinician to routinely perform the procedure percutaneously. The subclavian/axillary artery is considered a backup access site when the femoral artery and/or associated pathway to the aortic valve precludes delivery due to tortuosity, heavy calcification, and/or vascular disease. The subclavian/axillary artery is a backup access site since it generally requires a surgical cutdown procedure, unlike the femoral artery which can be accessed percutaneously. In other ways, however, subclavian artery access for a TAVI procedure has distinct advantages over a TAVI procedure using femoral access. For example, and not by way of limitation, subclavian artery access for TAVI procedures allows for better control of the delivery catheter and the bioprosthesis during delivery. Subclavian artery access for TAVI procedures also eliminates the need for any groin sticks since all intervention can be accomplished above the waist. This latter advantage enables patients to potentially become mobile sooner than with the femoral access procedures. Disadvantages of subclavian access for procedures include difficulty in accessing and closing the subclavian artery that is significantly less superficially located (i.e., deeper) than the femoral artery. As noted above, accessing the subclavian artery normally requires a surgical cut-down procedure. Also, while the access point to the femoral artery can normally be closed by compression (such as a weight placed in the access region), access to the subclavian artery cannot be closed with compression due to the depth of the artery and the location of the clavicle. Thus, a surgical technique is normally required to close the access point of the subclavian artery, such as the use sutures to close the access hole/arteriotomy.

Accordingly, it would be desirable to provide percutaneous access to the subclavian artery in order to take advantage of the advantages provided by access via the subclavian artery while eliminating the disadvantages due to the current lack of percutaneous access via the subclavian artery and difficulties in closing access to the subclavian artery. Facilitating a percutaneous subclavian/axillary artery access for TAVI procedures may result in improved TAVI outcomes as well as providing an even more competitive alternative for sites performing transapical TAVI procedures.

BRIEF SUMMARY OF THE INVENTION

Embodiments hereof relate to a method of accessing and closing a vessel. In one embodiment, a vessel is percutaenously accessed through a first opening in the vessel wall at a first location. A stent-graft is delivered in a radially compressed configuration through the first opening to a second location spaced from the first location. The stent-graft includes a plurality of stents, graft material coupled to the stents, a first end, a second end, a lumen, and a fenestration through the graft material between the first end and the second end. The stent-graft is deployed at the second location such that the stent-graft expands from the radially compressed configuration to a radially expanded configuration. The vessel is then accessed through a second opening through the vessel wall at the second location, wherein the second opening is generally aligned with the fenestration in the stent-graft such that the lumen of the stent-graft can be accessed through the second opening and the fenestration. A delivery device is advanced through the second opening, the fenestration, and the stent-graft lumen to a third location spaced from the first location and the second location. After a procedure at the third location, the delivery device is retracted through the lumen of the stent-graft and out of the fenestration and the second opening in the vessel wall. The stent graft is then rotated or translated such that the fenestration is not aligned with the second opening.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms “distal” and “proximal” are used in the following description with respect to a position or direction relative to the treating clinician. “Distal” and “distally” are positions distant from or in a direction away from the clinician, and “proximal” and “proximally” are positions near or in a direction toward the clinician. For the stent-graft prosthesis “proximal” is the portion nearer the heart by way of blood flow path while “distal” is the portion of the stent-graft further from the heart by way of blood flow path. In addition, the term “self-expanding” is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of percutaneous access to the left subclavian artery for transcatheter aortic valve implantation procedures, the invention may also be used in any other body passageways and for other procedures where it is deemed useful. Furthermore, there is no intention to be bound by any expressed or implied theory presented in the preceding technical field, background, brief summary or the following detailed description.

Figure 1:
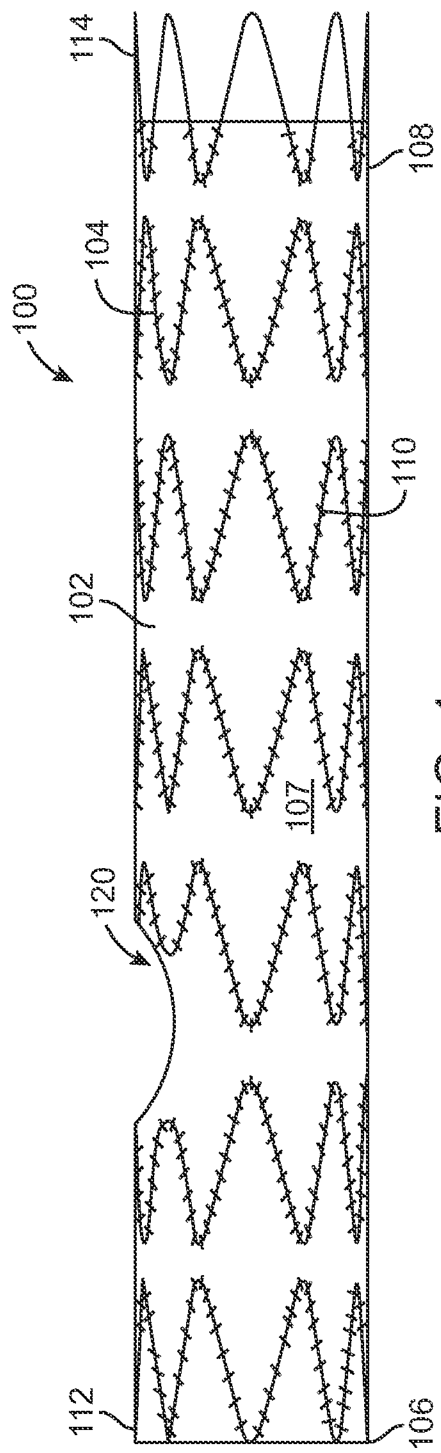
FIG. 1 is a schematic side view of stent-graft to support a vessel for percutaneous access to the vessel.
Figure 2:
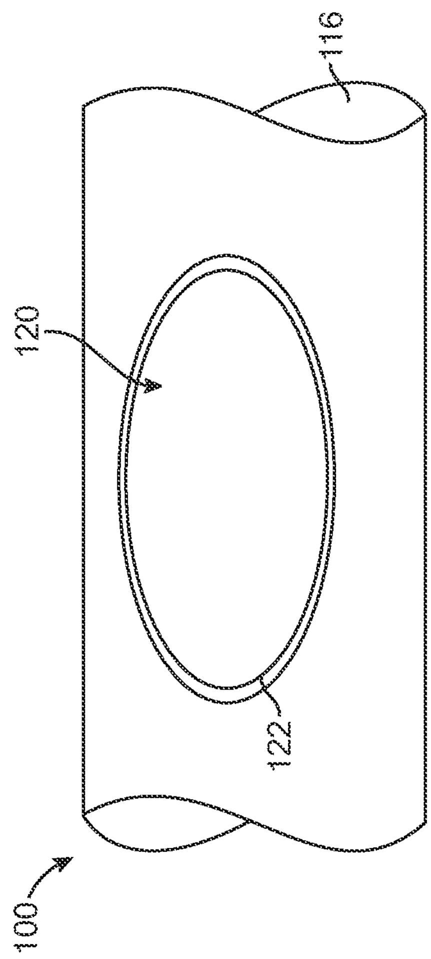
FIG. 2 is a top view of a portion of the stent-graft of FIG. 1.
Figure 3:
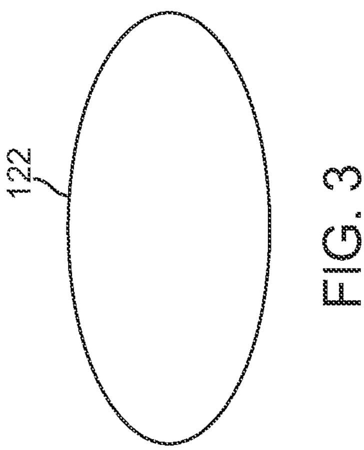
FIG. 3 is schematic side view of a radiopaque ring disposed around a fenestration of the stent-graft of FIG. 1.

With reference to FIGS. 1-3, a stent-graft 100 is configured for placement in a vessel such as the sublavian artery. Stent-graft 100 includes graft material 102 coupled to stents 104. Graft material 102 may be coupled to stents 104 using stitching 110 or other means known to those of skill in the art. In the embodiment shown in FIGS. 1-3 stents 104 are coupled to an outside surface of graft material 102. However, stents 104 may alternatively be coupled to an inside surface of graft material 102. Graft material 102 may be any suitable graft material, for example and not limited to, woven polyester, DACRON material, expanded polytetrafluoroethylene, polyurethane, silicone, or other suitable materials. Stents 104 may be any conventional stent material or configuration. As shown, stents 104 are preferably made from a shape memory material, such as thermally treated stainless steel or nickel-titanium alloy (nitinol), and are formed into a zig-zag configuration. Stent-graft 100 includes a proximal end 106, a distal end 108, and a body 107 therebetween. Proximal stent 112 and distal stent 114 may or may not extend beyond the ends of the graft material 102. In the embodiment shown, proximal stent 112 does not extend beyond a proximal end of the graft material and distal stent 114 does extend beyond a distal end of the graft material 102. Body 107 has a lumen 116 disposed therethrough. Stent-graft 100 further includes a fenestration 120, described in detail below. Stent graft-100 may be a variation of conventional thoracic stent grafts, such as Medtronic, Inc.'s VALIANT® thoracic stent-graft, or other known stent-grafts.

Fenestration 120 is disposed through a side surface of stent-graft 100 and is an opening through graft material 102. Fenestration 120 may be any shape, but is preferably round or oval in shape. Fenestration 120 is sized and shaped such that a catheter utilized for a procedure such as a transcatheter aortic valve implantation may extend through fenestration 120. For example, and not by way of limitation, fenestration 120 may have a long axis of approximately 6-12 mm and a short axis of approximately 4-10 mm. Similarly, a circular fenestration may have a diameters in the range of 6-12 mm. However, those skilled in the art would recognize that the size of fenestration 120 can be selected to be slightly larger than the catheter or introducer to be inserted therethrough. A radiopaque ring 122 is disposed around fenestration 120. Radiopaque ring 122 provides a target for percutaneous access through the vessel and stent-graft 100, as describe in more detail below. Radiopaque ring 122 may be made of materials generally considered radiopaque by those skilled in the art. For example, and not by way of limitation, radiopaque ring may be made from tantalum, tungsten, molybdenum, niobium, rhenium, carbon, germanium, silicon, and other materials known to those skilled in the art as radiopaque, and alloys thereof. For the purposes of this disclosure, radiopaque will refer to those substances or materials which have suitable visibility for percutaneous procedures when being imaged by an X-ray imaging device such as but not limited to a fluoroscope. Radiopaque ring 122 may be coupled to graft material 102 using stitches or other similar coupling means. For example, and not by way of limitation, graft material 102 may be folded over radiopaque ring 122 and the folded over portion of the graft material 102 may be stitched to itself to capture radiopaque ring 122.

Figure 4:
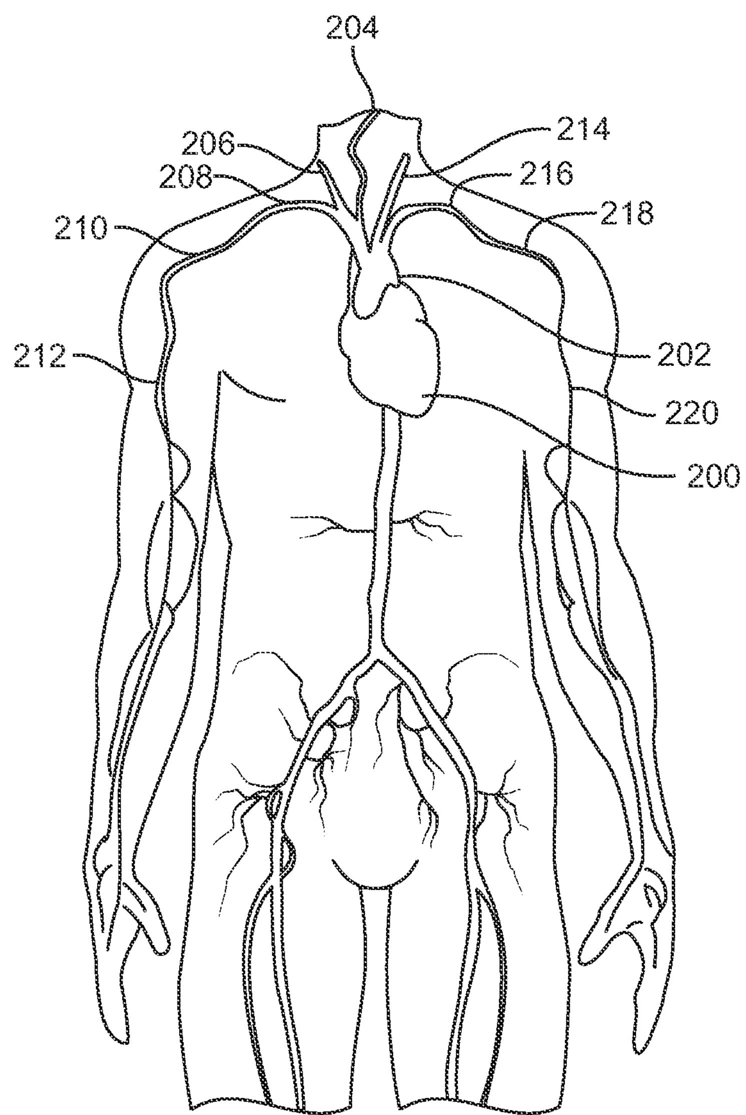
FIG. 4 is a schematic of a human heart and arteries of the upper body and upper limbs.

FIG. 4 is a schematic illustration of the arteries of the upper body and upper limbs of a human. In particular, FIG. 4 shows a heart 200 with an aorta extending from the left ventricle of heart 200. The aorta bends to form an aortic arch 202 and extends to the descending or thoracic aorta to the abdominal aorta. Emanating from the aortic arch 202 are three branch arteries, the innominate or brachiocephalic artery 204, the left common carotid artery 214, and the left subclavian artery 216. The brachiocephalic artery 204 branches into the right common carotid artery 206 and the right subclavian artery 208. The right subclavian artery 208 becomes the right axillary artery 210 in the right armpit region of the body, and extends to become the right brachial artery 212 in the right upper arm. The left subclavian artery 216 becomes the left axillary artery 218 in the left armpit region of the body, and extends to become the left brachial artery 220 in the left upper arm.

FIGS. 5-19B show schematically an example of method for accessing a vessel for delivery of an interventional device through the vessel, and subsequent closing of the access opening through a wall of the vessel. In the embodiment shown, the method is shown and described with respect to access through the left brachial artery 220 to deliver stent-graft 100 to a desired location in the left subclavian artery 216, and subsequent access through the wall of the left subclavian artery 216 and fenestration 120 in stent-graft 100 to deliver the interventional device to a desired location. However, those of ordinary skill in the art would understand that the method is not limited to the particular location described. In particular, but not by way of limitation, access for delivery of stent-graft 100 may be through the right brachial artery 212 to the right subclavian artery 208 for subsequent access through the wall of the right subclavian artery 208 and fenestration 120 of stent-graft 100 for delivery of the interventional device. Further, access through the subclavian artery may be through the axillary artery. Since the axillary artery is an extension of the subclavian artery, the terms may be used interchangeably herein. The devices and methods may also be used at other locations.

Figure 5:
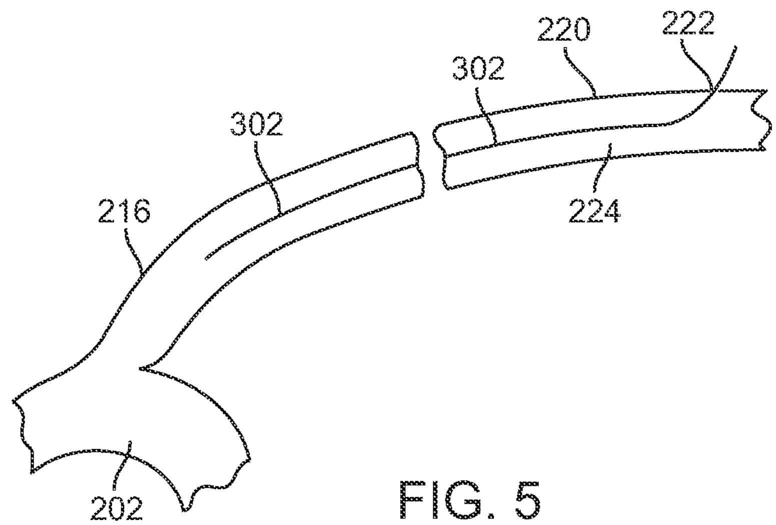
FIGS. 5-19B are schematic illustrations of a method for perutaneous access and closure of a vessel utilizing the stent-graft of FIG. 1.

FIG. 5 is a schematic drawing showing the step of accessing the left brachial artery 220 through an opening or arteriotomy 222 through the wall of the left brachial artery 220. This step can be accomplished through methods known to those of ordinary skill in the art, such as, but not limited to, the Seldinger technique. A guidewire 302 is advanced through arteriotomy 222 through a lumen 224 of brachial artery 220, left axillary artery 218 (not shown in FIG. 5), and into the left subclavian artery 216.

Figure 6:
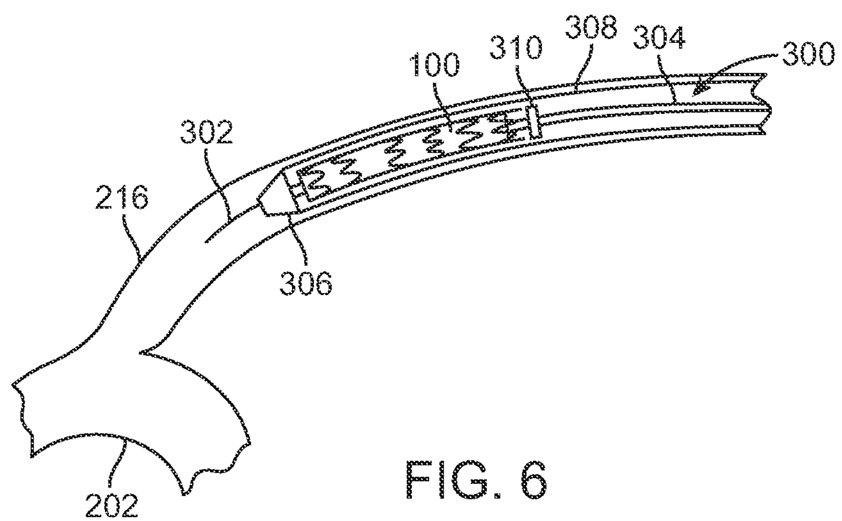

A stent-graft delivery system 300 is then advanced over guidewire 302 from arteriotomy 222 to a desired location in the left subclavian artery 216, as shown in FIG. 6. Although the location is shown in left subclavian artery 216, the location may be near where the left subclavian artery becomes the left axillary artery 218 or may be in the left axillary artery 218. Delivery system 300 may be any delivery system known to those of ordinary skill in the art that can deliver a stent-graft to a desired location. Described generally, delivery system 300 includes a tapered tip 306 that is flexible and able to provide trackability in tight and tortuous vessels. Other tip shapes such as bullet-shaped tips could also be used. The tip 306 includes a lumen disposed therethrough for accommodating guidewire 302. A sleeve 308 of stent-graft delivery system 300 extends over stent-graft 100 and abuts against a proximally facing surface of tip 306. Delivery system 300 also includes an inner tube or shaft 304 that is coupled to the tip lumen such that guidewire 302 may extend the length of delivery system 300. A stop 310 is located at a distal end of stent-graft 100 when stent-graft 100 is loaded onto the delivery system 300. Stop 310 prevents longitudinal movement of stent-graft 100 as sleeve 308 is retracted or otherwise removed to release stent-graft 100. Stent-graft 100 is disposed within sleeve 308 in a compressed or delivery configuration wherein the diameter of stent-graft 100 is reduced such that it can be inserted through the vasculature.

Figure 7:
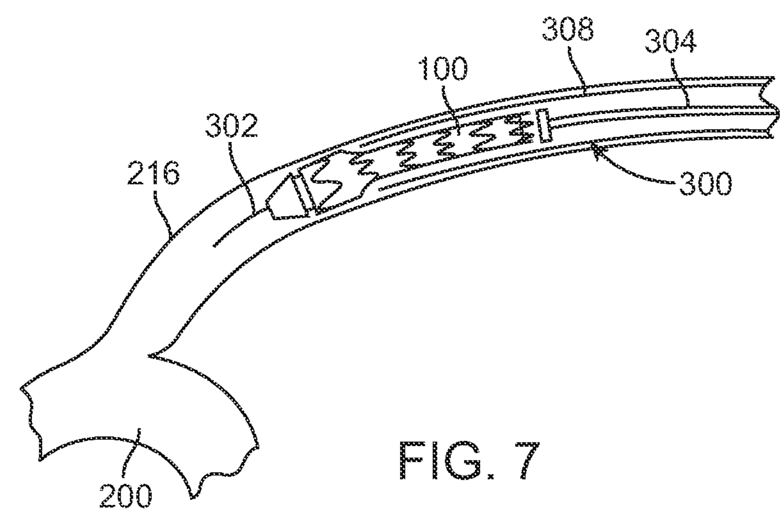
Figure 8:
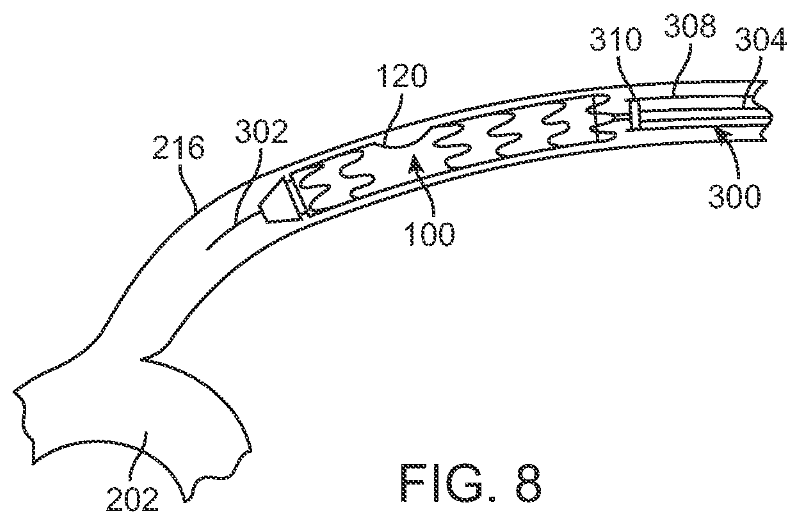
Figure 9:
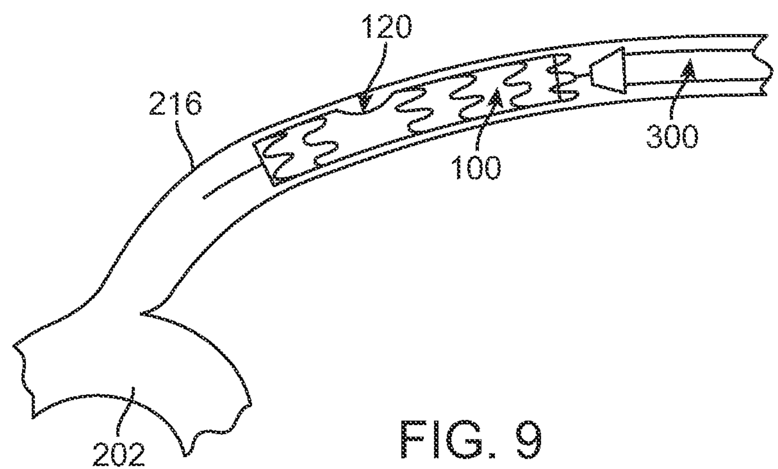

Once delivery system 300 is in the desired location, sleeve 308 is retracted proximally, as shown in FIG. 7. As sleeve 308 is retracted, the proximal end of stent-graft 100 begins to expand. As sleeve 308 is further retracted proximal to distal end of stent-graft 100, stent-graft 100 fully expands, as shown in FIG. 8. With stent-graft 100 fully expanded, fenestration 120 faces a wall of left subclavian atrery 216, as shown in FIG. 9. Delivery system 300 may be removed or may remain partially coupled to stent-graft 100 to re-position stent-graft 100 after the interventional procedure is completed, as described in more detail below.

Figure 10:
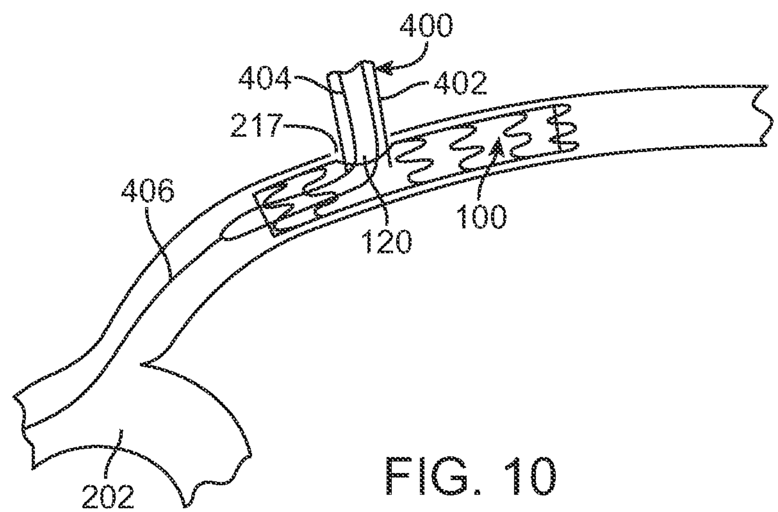

With stent-graft 100 in the desired location, an access opening or arteriotomy 217 is formed through a wall of left subclavian artery 216 in alignment with fenestration 120 of stent-graft 100, as shown in FIG. 10. An interventional delivery device 400, such as a device for delivering and deploying an aortic valve in a transcatheter aortic valve implantation (TAVI) procedure, is inserted into arteriotomy 217. Such delivery devices are known to those skilled in the art. For example, and not by way of limitation, interventional delivery device 400 may be the Medtronic CoreValve Delivery Catheter System, with or without the AccuTtrak™ Stability Layer, as described at http://www.medtronic.com/corevalve/ous/downloads/201006136_EE.pdf, or the delivery systems described in U.S. Patent Application Publication Nos. 2011/0251680 and 2011/0264201, the teachings of each of which are incorporated herein by reference. The delivery device 400 may be for delivery and implanting a stented prosthetic valve, such as, a prosthetic valve sold under the trade name CoreValve® available from Medtronic CoreValve, LLC. Other non-limiting examples of transcatheter heart valve prostheses useful with systems and methods of the present disclosure are described in U.S. Patent Application Publication Nos. 2006/0265056; 2007/0239266; and 2007/0239269, the teachings of each of which are incorporated herein by reference. With stent-graft 100 providing support for the left subclavian artery 216 and radiopaque ring 122 providing a target location within the subclavian artery 216, a Seldinger or modified technique may be used to gain access to the left subclavian artery. Other methods of gaining access to the left subcalvian artery, such as a cut-down procedure described in a brochure at http://www.medtronic.com/corevalve/ous/downloads/201104711aEE.pdf may also be used. Additional devices, such as an introducer or dilator 402, as known to those skilled in the art may also be used for delivery device 400 to gain access through arteriotomy 217.

Figure 11:
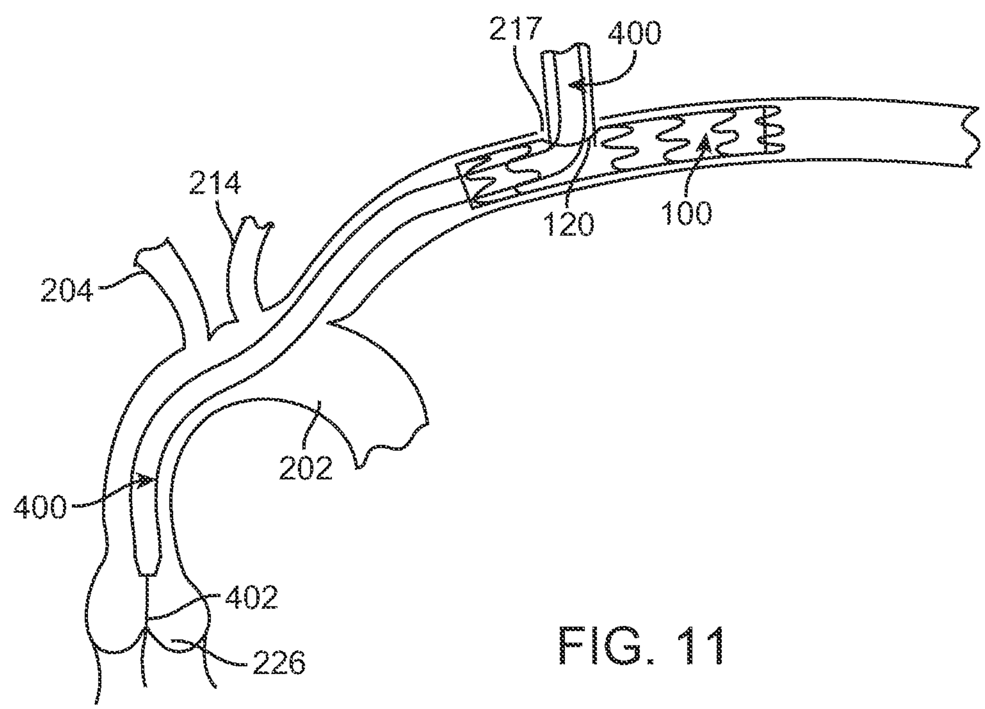
Figure 12:
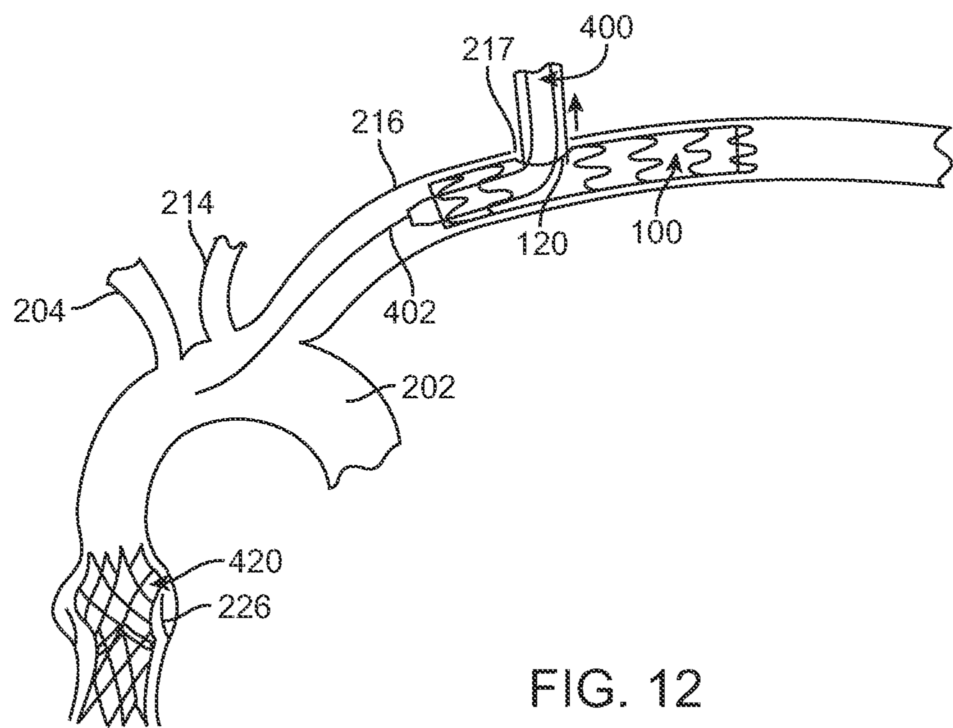

After interventional delivery system 400 is inserted through arteriotomy 217, it is advanced along a guidewire 402 to the desired site, as shown schematically in FIG. 11. In the present non-limiting example, interventional delivery device 400 is advanced to the site of the aortic valve 226 such that a prosthetic heart valve 420 may be implanted by methods known to those skilled in the art, after prosthetic heart valve 226 is implanted, interventional delivery device 400 may be retracted and removed from subclavian artery 216 through arteriotomy 217. FIG. 12 shows schematically delivery device 400 partially retracted after prosthetic heart valve 420 has been implanted.

Figure 13:
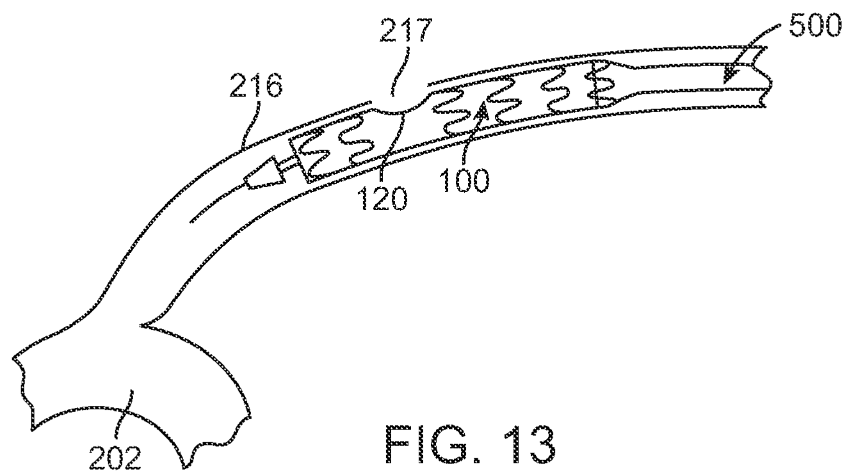
Figure 14:
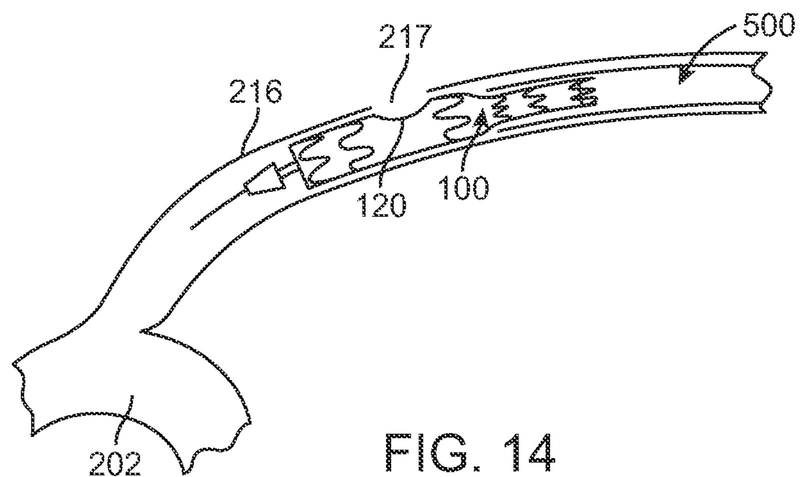

After interventional delivery device 400 is removed, a recapture catheter or device 500 may be advanced from the brachial artery 220 to the subclavian artery 216, adjacent to the distal end 108 of stent-graft 100, as shown schematically in FIG. 13. Recapture device 500 may be the same as stent-graft delivery system 300 or may be a different device. Recapture device 500 may be any recapture device known to those skilled in the art. For example, and not by way of limitation, recapture device 500 delivery catheter may be as described in U.S. Pat. Nos. 5,843,167; 5,902,334; and 5,961,546, the teachings of each of which is incorporated in its entirety by reference herein. Recapture device 500 recaptures stent-graft 100 such that stent-graft 100 is converted from the radially expanded configuration to a radially compressed configuration, as shown in FIGS. 13-15.

Figure 16:
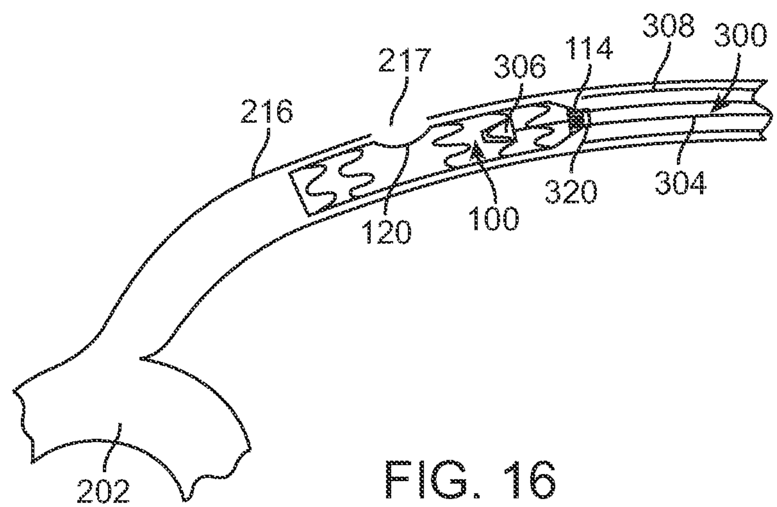
Figure 17:
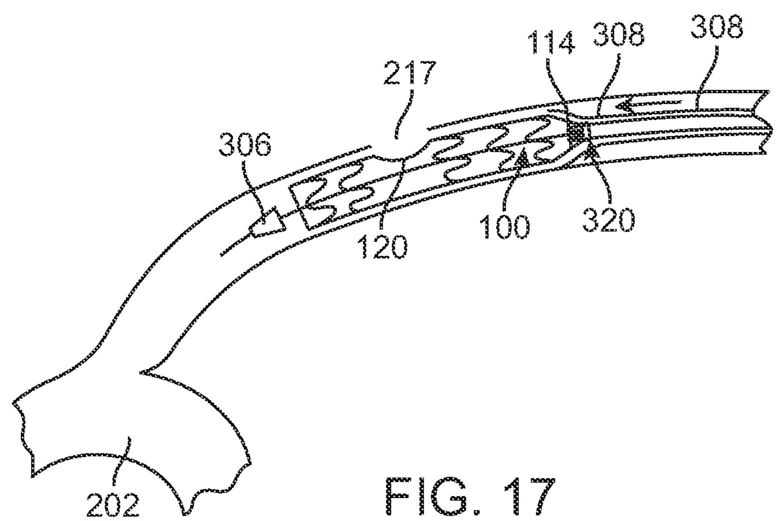

Further, instead of stent-graft delivery system 300 being completely withdrawn after stent-graft 100 is implanted, a capture mechanism 320 may maintain control of distal stent 114 of stent-graft 100 after stent-graft 100 is deployed. In such a situation, distal stent 114 may not fully deploy. For example, and not by way of limitation, the capture devices described in U.S. Patent Application Nos. 2008/0262590 and 2011/0251664, each of which is incorporated by reference herein in its entirety, may be used to maintain control of distal stent 114 of stent-graft 100 after sleeve 308 has been fully retracted. In such a method, after sleeve 308 has been retracted, distal stent 114 remains captured by a capture mechanism. Tip 306 may be partially retracted past fenestration 120 such that interventional delivery device 400 may be inserted through fenestration 120 and advanced to the treatment site. Upon withdrawal of interventional delivery device 400, tip 306 may be advanced distally beyond proximal end 106 of stent-graft 100 and sleeve 308 may be advanced distally over stent graft 100 to recapture stent-graft 100, as shown in FIGS. 16-18.

Figure 15:
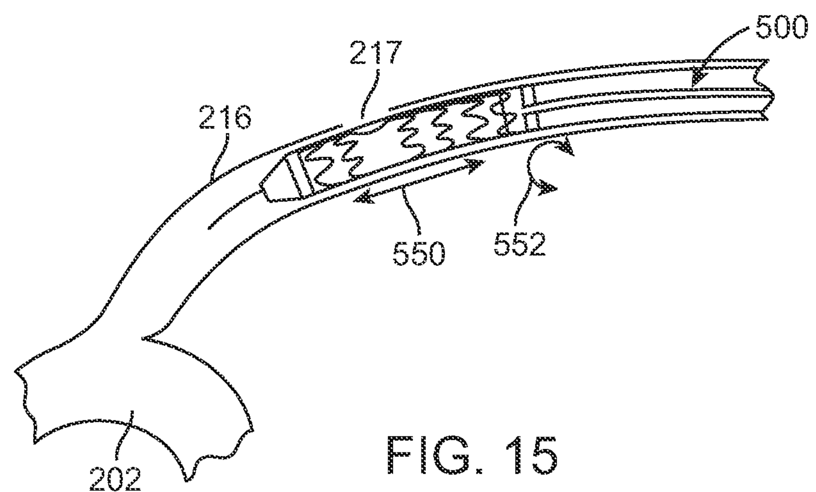
Figure 18:
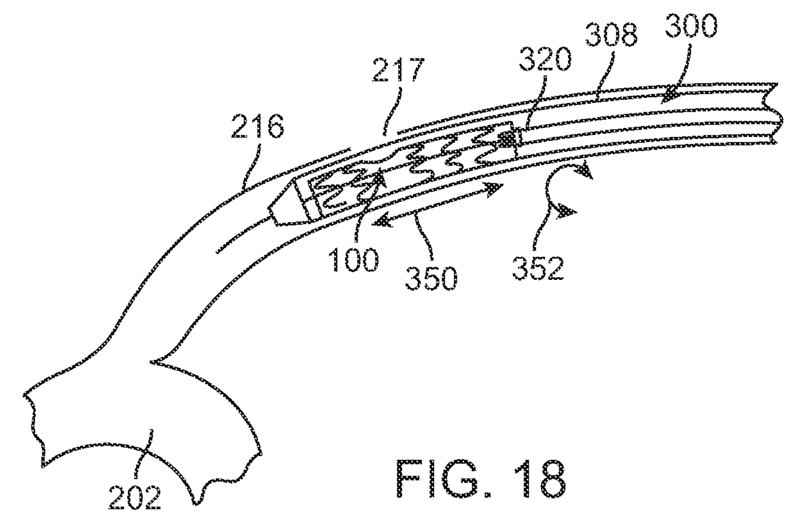

As shown schematically in FIGS. 15 and 18, after stent-graft 100 is recaptured within recapture device 500 or delivery system 300, recapture device 500 or delivery system 300 may either be translated as shown by arrows 550/350 or rotated as shown by arrows 552/352. After stent-graft 100 has been translated or rotated, stent-graft can be released from recapture device 500 or delivery system 300. If delivery system is used, capture mechanism 320 may also be released to fully deploy stent-graft 100. If recapture device 500 or delivery system 300 is rotated, stent-graft 100 is also rotated such that fenestration 120 is not aligned with arteriotomy 217, a shown in FIG. 19A. Thus, a portion of graft material 102 of stent-graft 100 covers arteriotomy 217 such that blood cannot escape through arteriotomy 217. Similarly, if recapture device 500 or delivery system 300 is translated, stent-graft

Figure 19A:
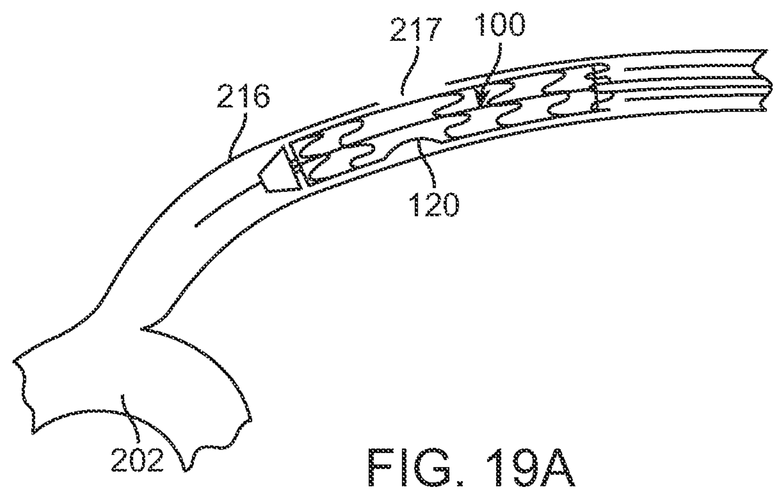
Figure 19B:
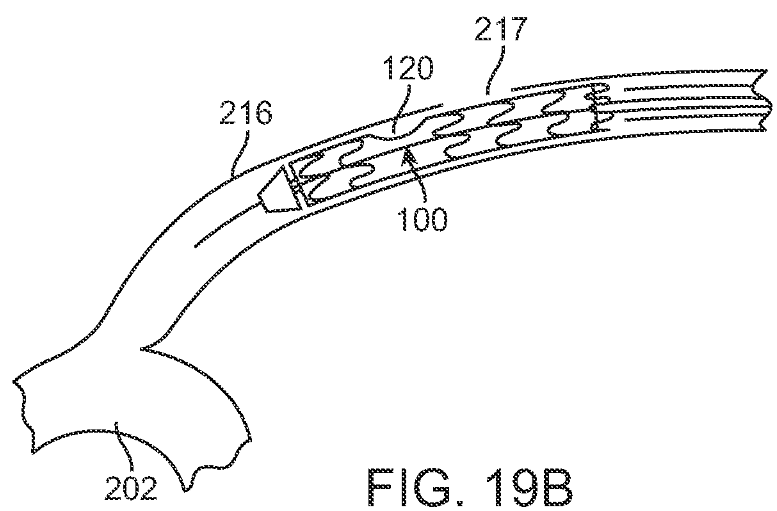

100 is also translated such that fenestration 120 is not aligned with arteriotomy 217, as shown in FIG. 19B. Thus, a portion of graft material 102 of stent-graft 100 covers arteriotomy 217 such that blood cannot escape through arteriotomy 217. This alleviates the need to suture arteriotomy 217.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, in the above embodiments, the scaffolding or support of the stent-graft prostheses have been illustrated as a series of independent or separate self-expanding stents/sinusoidal patterned rings. However, as will be understood by those of ordinary skill in the art, the support structure or scaffolding of a stent-graft prosthesis may have other configurations such as a series of sinusoidal patterned rings coupled to each other to form a self-expanding stent. In another embodiment, the support structure or scaffolding of a stent-graft prosthesis may be a unitary tubular component having diamond-shaped opening, which may be formed by various conventional stent forming methods as would be understood by one of ordinary skill in the art. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method for accessing a vessel comprising the steps of:

percutaneously accessing a vessel through a first opening in a wall of the vessel at a first location;

delivering a stent-graft in a radially compressed configuration through the first opening to a second location spaced from the first location, wherein the stent-graft includes at least one stent, graft material coupled to the at least one stent, a first end, a second end, a lumen, and a fenestration through the graft material between the first end and the second end;

deploying the stent-graft at the second location such that the stent-graft expands from the radially compressed configuration to a radially expanded configuration;

accessing the vessel through a second opening in the vessel wall at the second location, wherein the second opening is generally aligned with the fenestration in the stent-graft such that the lumen of the stent-graft can be accessed through the second opening and the fenestration;

advancing a delivery device through the second opening, the fenestration, and the stent-graft lumen to a third location spaced from the first location and the second location;

retracting the delivery device through the lumen of the stent-graft and out of the fenestration and the second opening; and rotating or translating the stent-graft such that the fenestration is not aligned with the second opening.

2. The method of claim 1, wherein a stent-graft delivery device is used to deliver the stent-graft from the first location to the second location.

3. The method of claim 2, wherein the stent-graft is disposed within a sleeve of the stent-graft delivery device in the radially compressed configuration and the sleeve is retracted to deploy the stent graft from the radially compressed configuration to the radially expanded configuration.

4. The method of claim 2, wherein the step of rotating or translating the stent-graft comprises the steps of:

recapturing the stent-graft such that the stent-graft is radially compressed from the radially expanded configuration to a second radially compressed configuration;

rotating or translating the stent-graft while in the second radially compressed configuration; and expanding the stent-graft from the second radially compressed configuration to a second radially expanded configuration such that the fenestration is not aligned with the second opening.

5. The method of claim 4, wherein a recapture catheter is used to recapture the stent graft.

6. The method of claim 5, wherein the recapture catheter and the stent-graft delivery device are the same device.

7. The method of claim 6, wherein the step of deploying the stent-graft at the second location such that the stent-graft expands from the radially compressed configuration to the radially expanded configuration comprises the stent-graft delivery device maintaining control of a distal stent of the stent-graft.

8. The method of claim 1, wherein the first opening is through a wall of the left brachial artery.

9. The method of claim 8, wherein the second opening is through a wall of the left subclavian artery or the left axillary artery.

10. The method of claim 9, wherein the third location is adjacent the aortic valve.

11. The method of claim 10, wherein after the step of advancing the delivery device to the third location, a prosthetic aortic valve is deployed from the delivery device.

12. The method of claim 1, wherein the first opening is through a wall of the right brachial artery.

13. The method of claim 12, wherein the second opening is through a wall of the right subclavian artery or the right axillary artery.

14. The method of claim 13, wherein the third location is adjacent the aortic valve.

15. The method of claim 14, wherein after the step of advancing the delivery device to the third location, a prosthetic aortic valve is deployed from the delivery device.

16. The method of claim 1, wherein a radiopaque ring is coupled to the graft material around a periphery of the fenestration.

17. The method of claim 16, wherein a portion of the graft material around the fenestration is folded over the radiopaque ring and the graft material is stitched to itself to capture the radiopaque ring.

* * * * *